United States Patent [19]

Boyer et al.

[11] Patent Number: 5,399,484
[45] Date of Patent: Mar. 21, 1995

[54] USE OF BLOCKING PROTEIN WITH HIGH PH EXTRACTION IN METHOD TO DETERMINE A MICROORGANISM ASSOCIATED WITH PERIODONTAL DISEASE AND KIT USEFUL THEREFOR

[75] Inventors: Bradley P. Boyer; Paul B. Contestable; Brian A. Snyder, all of Rochester, N.Y.

[73] Assignee: Eastman Kodak Company, Rochester, N.Y.

[21] Appl. No.: 773,064

[22] Filed: Oct. 8, 1991

[51] Int. Cl.$^6$ ............................................. G01N 33/569
[52] U.S. Cl. .................... 435/7.32; 435/7.92; 435/7.94; 435/961; 435/962; 435/975
[58] Field of Search ................ 435/7.32, 7.36, 7.92, 435/961, 962, 975, 7.94

[56] References Cited

U.S. PATENT DOCUMENTS

| | | | |
|---|---|---|---|
| 4,617,264 | 10/1986 | Whiteley et al. | 435/34 |
| 4,725,556 | 2/1988 | Mareschal et al. | 436/500 |
| 4,866,167 | 9/1989 | Chen et al. | 536/27 |
| 4,914,031 | 4/1990 | Zukowski et al. | 435/222 |
| 5,122,449 | 6/1992 | Gilbert et al. | 435/5 |

FOREIGN PATENT DOCUMENTS

| | | | |
|---|---|---|---|
| 269388 | 6/1988 | European Pat. Off. | 435/7.32 |
| 363089 | 4/1990 | European Pat. Off. | |
| 363110 | 4/1990 | European Pat. Off. | |
| 61/242596 | 10/1986 | Japan . | |
| 1560570 | 2/1980 | United Kingdom . | |
| 2099578 | 12/1982 | United Kingdom | 435/7.31 |
| 89/00695 | 1/1989 | WIPO . | |
| 1/01154 | 2/1989 | WIPO . | |

OTHER PUBLICATIONS

Microparticle Immunoassay Techniques. 2nd Ed., Seradyn, Inc. (1988) pp. 1–49.
Gmur et al, "Monoclonal Antibodies to Characterize the Antigenic Heterogeneity of *Bacteroides intermedius*" in Monoclonal Antibodies against Bacteria, Macavio et al, eds pp. 91–119 (1985).
Zambon et al, Oral Microbiol. Immunol. 1:39–44 (1986).
Stockman et al, J. Clin. Microbiol., 16(5), pp. 965–967 (1982).
Nesbitt et al, Biol. Abstr., 70, 44699 (Abstract only).

*Primary Examiner*—Carol E. Bidwell
*Attorney, Agent, or Firm*—James L. Tucker

[57] ABSTRACT

A method has been developed for determining microorganisms associated with periodontal diseases which is highly sensitive and shows very low background and cross-reactivity among various closely related antigens. Antigen is extracted at relatively high pH, and either before or immediately after extraction, the antigen-containing specimen is mixed with a blocking composition having at least about 0.2 weight percent of a non-immunoreactive blocking protein. The pH of the resulting mixture is kept high when contacted with the antibodies specific to the antigen of interest. The compositions and components needed for the assay can be supplied in a diagnostic test kit.

18 Claims, No Drawings

USE OF BLOCKING PROTEIN WITH HIGH PH EXTRACTION IN METHOD TO DETERMINE A MICROORGANISM ASSOCIATED WITH PERIODONTAL DISEASE AND KIT USEFUL THEREFOR

FIELD OF THE INVENTION

The present invention relates to a diagnostic test kit and a method for the determination of a microorganism associated with periodontal diseases. In particular, the method is useful for the differentiation of such microorganisms including the microorganisms *Actinobacillus actinomycetemcomitans*, *Prevotella intermedia* (formerly known as *Bacteroides intermedius*) and *Porphyromonas gingivalis* (formerly known as *Bacteroides gingivalis*).

BACKGROUND OF THE INVENTION

There is a continuous need in medical practice, research and diagnostic procedures for rapid, accurate and qualitative or quantitative determinations of biological substances which are present in biological fluids at low concentrations. For example, the presence of drugs, narcotics, hormones, steroids, polypeptides, prostaglandins or infectious organisms in blood, urine, saliva, vaginal secretions, dental plaque, gingival crevicular fluid and other biological specimens has to be determined in an accurate and rapid fashion for suitable diagnosis or treatment.

To provide such determinations, various methods have been devised for isolating and identifying biological substances employing specific binding reactions between the substance to be detected (sometimes identified as a "ligand") and a compound specifically reactive with that substance (sometimes identified as a "receptor").

Specific microorganisms have been implicated as indicators for a number of periodontal diseases in humans and animals, such as gingivitis and periodontitis. The importance of such diseases is growing in the human population, especially as people live longer, and prevention of such diseases is becoming of considerable importance to dentists, insurance carriers and the health industry in general. In addition, proper dental care for animals is a growing concern in our culture.

Detection of microorganisms associated with periodontal diseases has been accomplished using culture techniques, DNA probes and a number of immunological procedures, such as agglutination assays, enzyme linked immunosorbent assays (ELISA) and others known in the art. ELISA assays utilize the reaction of an extracted antigen from the microorganism(s) and the corresponding antibody to form an immunological complex. Usually uncomplexed materials are washed from the complex in order to provide an accurate assay result.

Extraction of antigen from microorganisms of interest in a biological specimen is generally critical to providing an accurate, rapid and sensitive assay. Many varied techniques have been used for extraction including physical disruption of the cells by sonication, heating or centrifugation. Chemical extraction compositions have also been developed. For example, various surfactants, such as sodium dodecyl sulfate, have been used individually in extraction compositions.

An advance in the art in the detection of microorganisms associated with periodontal diseases is described and claimed in U.S. Ser. No. 468,392 (filed Jan. 22, 1990 by Snyder). This case describes the simultaneous detection and differentiation of these microorganisms, and particularly *Actinobacillus actinomycetemcomitans*, *Porphyromonas gingivalis* and *Prevotella intermedia*, in an immunometric (also known as "sandwich") assay using water-insoluble reagents in defined regions of a microporous filtration membrane. The simultaneous detection and differentiation of these microorganisms have considerable clinical and commercial significance.

While the noted simultaneous assay represents an important advance in the art for detecting the noted microorganisms, in some cases, unacceptable background was observed, especially when clinical specimens were tested. It was also noticed that the known surfactant extraction composition did not adequately extract antigen from all serotypes of the microorganisms of interest. This problem was solved by using as an extraction composition, a high pH solution of a cationic surfactant mixed with a specific anionic surfactant. The details of this invention are provided in copending and commonly assigned U.S. Ser. No. 773,833, filed on even date herewith by Snyder, Contestable, Abrams and Grogan and entitled "Test Kit and Method for the Detection of Microorganisms Associated with Periodontal Diseases Using Surfactant Mixture As Extraction Composition" now U.S. Pat. No. 5,334,503.

Further improvements were provided by the use of certain wash solutions in such assays, as described in U.S. Ser. No. 774,019 (filed on even date herewith by Boyer, Contestable and Snyder), entitled "Wash Composition, Test Kit and Method for Determination of Microorganisms Associated with Periodontal Diseases" now U.S. Pat. No. 5,248,595.

However, further improvement is needed since in the assay of some clinical specimens to differentiate among microorganisms, false positives have been observed when one microorganism is present in relatively higher concentrations than the others being detected.

SUMMARY OF THE INVENTION

This problem has been overcome with a method for the determination of a microorganism associated with a periodontal disease comprising the steps of:

A. in a specimen suspected of containing a microorganism associated with a periodontal disease, extracting an antigen from the microorganism using an extraction composition which is buffered to a pH of at least about 8, B. prior to, simultaneously with or immediately after extraction in step A, mixing the extraction composition with a blocking composition consisting essentially of a non-immunoreactive blocking protein in an amount sufficient to provide a mixture having at least about 0.2 weight percent of the protein, the blocking properties of the protein not being adversely affected by the high pH of the mixture or any surfactant present therein, C. without lowering the pH of the mixture formed in step B below about 8, contacting the mixture with an antibody specific to the antigen to form an immunological complex, and D. detecting the complex as an indication of the determination of the microorganism in the specimen.

This invention also provides a diagnostic test kit comprising, in separate packaging:

(a) an extraction composition buffered to a pH of at least about 8, (b) a composition consisting essentially of a non-immunoreactive blocking protein, and (c) a water-soluble antibody specific for an antigen present in a microorganism associated with a periodontal disease.

This invention provides a rapid and sensitive method for determining a microorganism associated with periodontal diseases. More preferably, it provides a rapid and effective means for differentiating among a plurality of such microorganisms that are in the same test specimen. It is particularly useful in the differentiation of microorganisms associated with periodontal diseases in a single test device or test well. As noted above, it is quite important in certain diagnoses and treatment that discrimination among microorganisms be made. The present invention provides a means for that and particularly enables discrimination when one or more microorganisms are present in substantially higher concentrations than others being detected, while keeping background low and minimizing non-specific immunological reactions.

These advantages are possible by mixing antigen before or immediately after extraction at relatively high pH, with at least about 0.2% (by weight) of a non-immunoreactive blocking protein while maintaining the relatively high pH. The "blocking" protein apparently blocks nonspecific interactions that would obscure accurate signals in the immunoassay. A particularly useful non-immunoreactive protein is a protease, but many proteases are adversely affected by high pH and high concentrations of surfactants commonly used in assays. Thus, the non-immunoreactive blocking protein (whether protease or another protein) used in the present invention must have blocking properties which are not adversely affected by the high pH of or surfactants in the extraction composition.

DETAILED DESCRIPTION OF THE INVENTION

The present invention can be used to rapidly and sensitively determine the presence of one or more microorganisms associated with periodontal diseases. In particular, the microorganisms *Actinobacillus actinomycetemcomitans*, *Porphyromonas gingivalis* and *Prevotella intermedia* can be determined or differentiated, either individually or collectively, using the present invention. However, other microorganisms which are suspected of being associated with periodontal diseases can also be detected or differentiated from each other with this invention. Such other microorganisms include, but are not limited to, *Wolinella recta*, *Bacteroides forsythus*, *Eikenella corrodens*, *Fusobacterium nucleatum* and *Treponema denticola*. In some embodiments of this invention, it is irrelevant as to which serotypes of any of the microorganisms may be present. In other embodiments, the invention can be used to differentiate among serotypes of a single species as well as among species.

The method of this invention is generally qualitative although the amount of immunological complex can be observed and correlated to the amount of microorganism in a specimen. Thus, the assay can be quantitative also. While the intact microorganisms can be detected with this invention, it is preferred to extract a detectable antigen (for example a lipopolysaccharide, capsule antigen or outer membrane protein) of interest from the host organism. Such antigens can be extracted from saliva, mucous from the throat or mouth, human or animal tissue extracts, gingival tissue, dental plaque or gingival crevicular fluid.

While antigen extraction from the noted microorganisms can be accomplished using suitable physical or chemical means such as with a detergent (for example sodium deoxycholate, sodium dodecyl sulfate or sodium decyl sulfate) following known procedures (see U.S. Pat. No. 4,741,999 issued May 3, 1988 to Genco et al), osmotic shock [see for example, Dirienzo et al, *Infect. & Immun.*, 47(1), pp. 31–36, 1985] or sonic means [see for example, Zambon et al, *Infect. & Immun.*, 41(1), pp. 19–27, 1983], the advantages of the present invention are available only if extraction is carried out at relatively high pH, that is at pH 8 or above.

A preferred extraction procedure is demonstrated below in relation to the examples using a high pH composition of a cationic surfactant and an anionic surfactant. Further details of this extraction procedure are provided in U.S. Ser. No. 773,833 (Snyder et al, noted above) now U.S. Pat. No. 5,334,503.

If desired, the extracted antigen can be removed from the original specimen, or the original specimen can be suitably diluted with buffer or water, or filtered in order to remove extraneous matter and to facilitate complexation of antigen with the corresponding antibody in the assay. However, it is an advantage of this invention that, whatever further treatment of the extracted antigen, it is mixed with the blocking composition containing the non-immunoreactive blocking protein (described below) without lowering the pH of the resulting mixture below about 8. If necessary, a suitable high pH buffer or base can be added to the mixture to keep the pH high. Preferably, the resulting mixture has a pH of from about 8.5 to about 11.5.

The extraction composition is mixed with the blocking composition described herein either before or after antigen extraction. Preferably, they are mixed after antigen is extracted. Mixing is generally carried out by adding one composition to the other at room temperature with modest agitation for a few seconds. Suitable base or high pH buffer can then be added to maintain high pH if desired.

Thus, extracted antigen is mixed at some point, at high pH, with one or more non-immunoreactive blocking proteins prior to antigen complexation with antibodies. Generally, the blocking proteins reduce or eliminate the cross reactivity at high concentrations of certain antigens, such as antigens extracted from *Prevotella intermedia* and *Porphyromonas gingivalis*. They are generally supplied in an aqueous buffered solution having a pH of from about 6 to about 11. The concentration of the protein in this buffered blocking solution can vary from about 0.4 to about 7 weight percent, and one skilled in the art can then determined how much should be used to provide a mixture with the antigen so that the protein is present in an amount of at least about 0.2 percent based on the total weight of the mixture. Preferably, the non-immunoreactive blocking protein is present in the resulting mixture with the extracted antigen in an amount of from about 0.2 to about 1 percent by weight.

Useful non-immunoreactive proteins include serum proteins (such as bovine serum albumin, fibrinogen and fibronectin), casein and other milk proteins, various enzymes such as proteases, and other proteins which could readily be tested to see if they provide the desired results. Such a test would include putting a suitable amount of the protein in a pH 8 solution of any appropriate surfactant (such as a mixture of a cationic surfactant and an anionic surfactant) for about 10 minutes to see if the protein is degraded, and then to use it as a blocking protein in an assay as described in Example 1 below. If the results of the assays show decreased or elimination of cross reactivity at high antigen concentration associated with high numbers of microbial cells (about $1 \times 10^8$ cells/ml), the protein is useful as a blocking protein.

Such proteins are "non-immunoreactive" because they do not complex specifically with either the antigen of interest or antibodies thereto.

Particularly useful blocking proteins include, but are not limited to, proteases which have the requisite stability at high pH and high surfactant concentration. Not just any protease has such qualities. Those that do can be obtained from any of a number of sources including microorganisms (such as bacteria and fungi), animal or human organs (such as the pancreas) and plants. Proteases can also be obtained from genetically altered microorganisms, and from a number of commercial sources.

Highly stable proteases are described in the literature, for example, in U.S. Pat. No. 4,914,031 (issued Apr. 3, 1990 to Zukowski et al). Generally such materials are subtilisin proteases which are analogs of a *Bacillus subtilis* protease having an amino acid sequence comprising one or more Asn-Gly amino acid sequences wherein one or both amino acid residues of the shorter sequence are deleted or replaced by a residue of a different amino acid, such as serine or aspartic acid. It is particularly desired that the asparagine residues (Asn) in either or both of positions 109 and 218 be replaced with serine residues. Further characterization of such stable proteases is found in the noted patent.

A most preferred protease has the characteristics noted above, but in addition has one or more amino acid residues in calcium binding sites present in the amino acid sequence replaced with a negatively charged amino acid. For example, the asparagine amino acid residue in the 76 position of the sequence can be replaced by aspartic acid to great advantage. The procedures for preparing such proteases are described in the noted patent.

One highly useful protease is marketed by Genencor International (Rochester, N.Y.) under the trademark AMIDEK 131.

The blocking composition has only the non-immunoreactive protein described above as an essential component, but it can include one or more optional components including salts such as sodium chloride and calcium chloride, sodium azide and diols such as propandiol (which is useful for promoting protease stability). A representative and preferred blocking composition is shown below in relation to the examples.

Without lowering the pH of the mixture of extracted antigen and non-immunoreactive protein (and perhaps by adding suitable high pH buffer or base to maintain the high pH), the mixture is then contacted with antibodies specific for the extracted antigen to form an immunological complex. This can be done in a variety of assay formats (described in more detail below).

Antibodies useful in the practice of this invention can be monoclonal or polyclonal. Monoclonal antibodies can be prepared using standard procedures, such as those described in U.S. Pat. No. 4,741,999 (noted above). Polyclonal antibodies can also be produced using standard procedures, such as described by Zambon et al, supra. Generally, a mammal is immunized one or more times with a suitable quantity of an antigenic component or whole bacterial cells of the organism. After a suitable time, when the titer is acceptable, antisera is recovered from the mammal. Antibodies can be removed from antisera and purified if desired using known procedures and stored in frozen buffered solutions until used. A preferred method for providing highly specific polyclonal antibodies is described in copending U.S. Ser. No. 468,393 (filed Jan. 22, 1990 by Reynolds et al). This method generally calls for injecting a mammal with an immunizing amount of an antigen a first time, injecting the mammal a second time between the second and fourteenth days after the first injection with a boosting amount of the antigen, and beginning the fifteenth day after the first injection, injecting the mammal at least three times every seven day period for at least four seven-day periods with a boosting amount of antigen. An immunizing amount and boosting amount can be readily determined by a skilled worker in the art. After the last booster injection, antisera is removed from the mammal.

The formation of an immunological complex of the antigen and antibody can be accomplished using any of a number of procedures and the present invention is not limited to a specific procedure even though the "sandwich" assays described in detail below are most preferred. See Rose et al (Eds.), *Manual of Clinical Laboratory Immunology*, 3rd Ed., American Society for Microbiology, Washington, D.C., 1986, Chapter 74 (Fucillo et al) for details of various immunological methods.

In one embodiment, the extracted antigen can be insolubilized by direct adsorption or covalent attachment to a solid substrate, such as polymeric or glass particles, filtration membranes, cellulosic filter papers, solid polymeric or resin-coated films, glass slides or walls of test tubes, glass or polymeric cuvettes and other substrates readily determinable by one of ordinary skill in the art. Such assays are generally known in the art as "direct binding" assays whereby the antigen directly binds to the substrate, and antibodies are used to complex with the insolubilized antigen. The antibodies can be detectably labeled to make the complex detectable, or the complex can be detected using an anti-antibody which is suitably labeled and specific to the first unlabeled antibody. Detection of the complex can be effected after washing using known techniques. Further details of how direct binding assays are carried out are provided for example in U.S. Pat. No. 4,497,899 (issued Feb. 5, 1985 to Armstrong et al) and copending and commonly assigned U.S. Ser. No. 468,045 (filed Jan. 22, 1990 by Snyder et al) now U.S. Pat. No. 5,212,061.

Another embodiment of the method of this invention is an agglutination method whereby antibodies to the extracted antigen are affixed to small particles in some manner and the particles which are detectable by light scattering or by the presence of a tracer such as dye or radioisotope within the particles. The resulting immunoreactive complex is formed through the reaction of antigen with antibodies on the particles, and can be detected using known procedures after washing. Technical details regarding agglutination assays are provided, for example in U.S. Pat. No. 4,847,199 (issued Jul. 11, 1989 to Snyder et al).

Examples of other useful assays include competitive immunoassays and enzyme-linked immunosorbent assays (commonly known as ELISA). Such assays are described generally in U.S. Pat. No. 4,427,782 (issued Jan. 24, 1984 to Caldwell et al) and by Schmeer et al, *J. Clin. Microbiol.*, 15(5), pp. 830–834 (1982).

A preferred embodiment of this invention is an immunometric or sandwich assay in which the extracted antigen is reacted at different epitopic sites with two antibodies, one of which is immobilized (or capable of being immobilized such as through avidin-biotin or other specific binding reactions) on a water-insoluble substrate, and a second antibody being water-soluble and detectably labeled. Suitable substrates on which one antibody is immobilized include those noted above for direct binding assays. Preferably, particulate carrier materials formed from organisms, natural or synthetic polymers, glass, ceramics, diatomaceous earth or magnetizable particles are used. These particles are more preferably polymeric, spherical in shape and have an average particle size (in largest dimension) of from about 0.01 to about 10 $\mu$meters, although the size, structural and spatial configurations are not critical. The general procedures for immunometric assays are described, for example, in U.S. Pat. No. 4,376,110 (issued Mar. 8, 1983 to David et al) and U.S. Pat. No. 4,486,530 (issued Dec. 4, 1984 to David et al).

The antibodies can be attached to particulate carrier materials to form water-insoluble immunological reagents by physical or chemical means, including adsorption or covalent reaction with reactive groups on the surface of the materials. Covalent attachment is preferred for optimal assay sensitivity. Many useful reactive groups are known in the art for antibody attachment, which groups can be part of the chemical structure of the carrier material, or added by coating or chemical treatment of an inert material. One skilled in the art would readily understand how to prepare such materials to have any of the following reactive groups: carboxy, 2-substituted ethylsulfonyl, vinylsulfonyl, epoxy, aldehyde, active halo atoms, amino, hydrazide and active esters such as succinimidoxycarbonyl.

Particularly useful particulate carrier materials are polymeric beads described, for example, in EP-A-0 323 692 (published Jul. 12, 1989) which are prepared from one or more ethylenically unsaturated polymerizable monomers having an active halo atom, activated 2-substituted ethylsulfonyl or vinylsulfonyl groups. Other particularly useful particles having reactive carboxy groups are described in copending U.S. Ser. No. 654,112 (filed Feb. 12, 1991 by Ponticello et al) now U.S. Pat. No. 5,149,737.

Homo- and copolymers described in EP-A-0 323 692 include the following representative materials: poly(m & p-chloromethylstyrene), poly(styrene-co-m & p-chloromethylstyrene-co-2-hydroxyethyl acrylate) (67:30:3 molar ratio), poly[styrene-co-m & p-(2-chloroethylsulfonyl-methyl)styrene] (96:4 molar ratio), poly{styrene-co-N-[m & p-(2-chloroethylsulfonylmethyl)-phenyl]acrylamide} (99.3:0.7 molar ratio), poly (m & p-chloromethylstyrene-co-methacrylic acid) (95:5 molar ratio), poly[styrene-co-m & p-(2-chloroethylsulfonyl-methyl)styrene-co-methacrylic acid] (93.5:4.5:2 molar ratio) and poly[styrene-co-4-(2-chloroethylsulfonylmethyl)styrene] (95.5:4.5 molar ratio).

Procedures for attaching antibodies to particles having reactive groups are well known, as described for example in U.S. Pat. No. 3,925,157 (issued Dec. 9, 1975 to Hamsher), U.S. Pat. No. 4,181,636 (issued Jan. 1, 1980 to Fischer), U.S. Pat. No. 4,703,018 (issued Oct. 27, 1987 to Craig et al) and EP-A-0 323 692. In general, the antibodies are mixed with the particles under suitable conditions depending upon the attachment form (adsorption, covalent or use of a linking group). A worker skilled in the art would readily know what conditions should be used for each procedure. For example, for attachment to particles having reactive halo atoms, activated 2-substituted ethylsulfonyl or vinylsulfonyl groups, the antibodies are generally mixed with the particles for up to 24 hours at a temperature of from about 20° to about 40° C. in a suspension buffered at a pH of from about 7 to about 10. If carboxy groups are used for attachment, the well known carbodiimide activators can be used, as well as carbomoylonium compounds which are described in EP-A-0 308 235 (published Apr. 22, 1989). Antibodies can be absorbed on particles by incubating particles and antibodies in suspension at suitable temperature for several hours.

More preferably, the immunological reagents described above are coated or deposited on a microporous filtration membrane which is inert to chemical or biological reactions. It is generally composed of one or more natural or synthetic substances which have sufficient integrity for reagents to react or be affixed thereto without loss of form or function. It is porous enough for filtration needed to remove substantially all uncomplexed materials from the complexes formed thereon. Useful membrane materials include, but are not limited to, porous natural or synthetic polymers, sintered glass, membranes of glass or polymeric films or fibers, ceramic materials, cellulosic materials and particulate structures composed of beads bound together with an adhesive or binder material. The membranes are generally flat, but some irregularities in the surfaces are acceptable, as well as some curvature if it is desired. One skilled in the art would be able to identify other useful materials which are commercially available or prepared using known techniques. Particularly useful materials are treated or untreated polyamide microporous membranes such as those commercially available from Pall Corp. under the trademarks LOPRODYNE and BIODYNE.

The membrane generally has an average pore size in the largest dimension of from 0.4 to about 5 meters, although smaller or larger pores would be acceptable as long as the complexes formed remain on the membrane and fluid drainage is not adversely affected.

If desired, the membrane can be coated with surfactant or non-immunoreactive protein (such as casein or succinylated casein), as known in the art to reduce nonspecific interactions or to promote desired filtration.

The water-insoluble immunological reagents having appropriate antibodies can be affixed to the membrane over its entire surface or in defined regions thereof. Affixation is accomplished using any mechanical means such as coating, dipping, printing or spraying or fixed by covalent means. Generally, they are coated and dried on the membrane prior to use. They can be used in admixture with hydrophilic binders to provide additional integrity to the coating.

The membrane can be hand held in the assay to provide sites for complexation of extracted antigen and the antibodies thereon. However, preferably, the membrane is disposed or mounted in a disposable test device or article having a suitable frame and structure for holding the membrane and fluid which is drained therethrough. Many such test devices are known in the art, including but not limited to those shown in U.S. Pat. No. 3,825,410 (issued Jul. 23, 1974 to Bagshawe), U.S. Pat. No. 3,888,629 (issued Jun. 10, 1975 to Bagshawe), U.S. Pat. No. 3,970,429 (issued Jul. 20, 1976 to Updike), U.S. Pat. No. 4,446,232 (issued May 1, 1984 to Liotta), U.S. Pat. No. 4,833,087 (issued May 23, 1989 to Hinckley), U.S. Pat. No. 4,847,199 (issued Jul. 11, 1989 to Snyder et al), U.S. Pat. No. 4,921,677 (issued May 1, 1990 to Hinckley et al) and U.S. Pat. No. 4,923,680 (issued May 8, 1990 to Nelson). Particularly useful test devices are those marketed by Eastman Kodak Company under the trademark SURECELL test devices.

Preferred test devices have three test wells designed for providing both negative and positive control results as well as a specimen test result. Each test well contains a membrane as described herein.

Once the water-insoluble complex of antigen and antibodies is formed (preferably on the membrane), the complex is washed with a suitable wash composition to remove uncomplexed materials prior to detection of the complex. Washing can be carried out with distilled water, a buffer or a buffered solution of a wide variety of surfactants as is known in the art. However, it has been found that certain anionic surfactants provide additional advantages in lowered backgrounds when used in combination with the present invention. This is seen below in Examples 1 and 2 whereby commonly sodium decyl sulfate is not as useful in washing as other anionic surfactants such as that identified by the trademark TERGITOL TM 4. Further details of this preferred wash composition are provided in U.S. Ser. No. 774,079 (of Boyer et al, noted above) now U.S. Pat. No. 5,248,595.

If the complex is on a substrate that does not allow fluid drainage (such as a nonporous film or glass slide or cuvette), the uncomplexed materials and fluid can be decanted off or otherwise removed. Where a membrane or filter is used, the fluid and uncomplexed materials flow through the membrane or filter and the complex of interest is left thereon.

Depending upon the means of detection, the water-insoluble complex can then be detected using a number of standard reagents and methods. For example, the complex may be detected without tracers or signal producing labels using light scattering techniques known in the art. Agglutinates can be similarly detected.

Preferably, however, whether the assay format is a direct binding assay or immunometric assay, the immunological complex is detected by means of a detectable label on an antibody. Such labels can include, but are not limited to enzymes, avidin, biotin, radioisotopes, fluorogens and chromogens. Radioisotopes, enzymes and biotin are preferred. Enzymes are more preferred and can be used to generate colorimetric, fluorometric or chemiluminescent signals which can be evaluated with the unaided eye or using standard spectrophotometric equipment to measure electromagnetic density, spectra or intensity. Useful enzymes include, but are not limited to peroxidase, urease, alkaline phosphatase, acid phosphatase, glucose oxidase, $\beta$-galatosidase and glucosidase. Alkaline phosphatase and peroxidase are preferred with peroxidase being most preferred.

For a given enzyme label, there are various known compositions which provide detectable colorimetric, fluorometric or chemiluminescent signals in the presence of the enzyme. For example, one preferred embodiment utilizes a dye-providing composition which provides a dye in the presence of the enzyme through one or more chemical reactions. A number of leuco dyes are known to be useful for this purpose where peroxidase is the label including those described in U.S. Pat. No. 4,089,747 (issued May 16, 1978 to Bruschi) and U.S. Pat. No. 4,670,386 (issued Jun. 2, 1987 to Babb et al). A preferred dye-providing composition is illustrated in the examples below.

Alternatively, the enzyme label can be used in one or more reactions to produce a chemiluminescent signal, such as described for example in U.S. Pat. No. 4,647,532 (issued Mar. 3, 1987 to Watanabe et al), U.S. Pat. No. 4,835,101 (issued May 30, 1989 to Kao et al), U.S. Pat. No. 4,729,950 (issued Mar. 8, 1988 to Kricka et al) and U.S. Pat. No. 4,598,044 (issued Jul. 1, 1986 to Kricka et al). Other labels besides enzymes can also be used to produce chemiluminescent signals.

In the preferred immunometric assay, at some point the antigen is contacted with a detectably labeled water-soluble antibody. This can occur prior to, simultaneously with or subsequent to the formation of the immunological complex, but generally prior to washing with the wash composition of this invention. Thus, the complex of antigen and two antibodies is left on the preferred membrane when uncomplexed materials are washed through. Following formation of this sandwich complex and washing, detection is carried out using reagents and procedures described generally above.

Positive or negative controls can be carried out simultaneously with assay of the specimen. Depending upon the signal being produced for detection, appropriate reagents can be added to stop signal production, for example by adding reagents to stop the formation of a dye or production of light by chemiluminescence. These materials are well known in the art.

In a preferred method for the determination of a microorganism associated with a periodontal disease, the method comprises the steps of:

A. extracting an antigen from a microorganism associated with a periodontal disease which is present in a specimen, using an extraction composition which is buffered to a pH of from about 8.5 to about 11.5, B. prior to, simultaneously with or immediately after the extraction in step A and without lowering the pH of the extraction composition below about 8, mixing the extraction composition with a blocking composition consisting essentially of a non-immunological blocking protein in an amount sufficient to provide a mixture having at least about 0.2 weight percent of the protein, the blocking properties of the protein not being adversely affected by the high pH of the mixture or any surfactant present therein, C. contacting the mixture formed in step B with a microporous filtration membrane having thereon, in a discrete zone of a surface of the membrane, a water-insoluble reagent comprising water-insoluble particles having affixed thereto antibodies specific to the extracted antigen, to form in the zone, a water-insoluble complex between the antibody and the extracted antigen on the membrane, D. prior to, simultaneously with or immediately subsequently to the contact in Step C, but after step B, contacting the extracted antigen with a detectably labeled, water-soluble second antibody specific to the extracted antigen so as to form a detectably labeled, water-insoluble sandwich complex specific for the microorganism, the complex being formed from both water-soluble labeled and water-insoluble antibodies with the extracted antigen in the zone on the membrane, E. simultaneously with or subsequently to step D, washing uncomplexed materials through the membrane, and F. detecting the labeled, water-insoluble sandwich complex in the zone on the membrane as a determination of the microorganism in the specimen.

More preferably, the method just described is useful for the simultaneous determination or differentiation of a plurality of such microorganisms wherein the membrane has a plurality of distinct and independent zones containing distinct water-insoluble reagents for each of the specific microbial antigens of interest. Thus, distinct sandwich complexes of each extracted antigen and its corresponding antibodies are formed in the distinct zones on the membrane. For example, any or all of the microorganisms *Actinobacillus actinomycetemcomitans, Prevotella intermedia* and *Porphyromonas gingivalis* can be determined in this manner.

The solution of non-immunoreactive blocking protein described herein as useful in the present invention can be supplied alone, or as part of a diagnostic test kit. Such a test kit is described above generally as having a number of individually packaged kit components including, but not limited to an extraction composition buffered to a pH of at least about 8. The kit can also comprise a water-soluble antibody (labeled or unlabeled) specific for extracted antigen, a disposable test device having an appropriate membrane (as described above) which preferably has an average pore size of from about 0.4 to about 5 μmeters, a wash composition to separate uncomplexed materials from complex of antigen and antibody, the wash composition generally including at least one surfactant, compositions for providing colorimetric, fluorometric or chemiluminescent signals in the presence of an enzyme label, instructions, pipettes and any other equipment or materials generally included in test kits.

The following examples are included to illustrate the practice of this invention, and are not meant to be limiting in any way. All percentages are by weight unless otherwise noted.

Materials for the Examples

SURECELL TM disposable test devices were used containing LOPRODYNE TM nylon microporous filtration membranes (1.2 μmeters average pore size) incorporated into the three test wells. The membrane was used without any further treatment.

Dye-providing composition A was prepared to include 4,5-bis (4-methoxyphenyl)-2-(3,5-dimethoxy-4-hydroxyphenyl)imidazole leuco dye (0.008%), poly(vinyl pyrrolidone) (1%), sodium phosphate buffer (10 mmolar, pH 6.8), hydrogen peroxide (10 mmolar), 4'-hydroxyacetanilide (0.5 mmolar) and diethylenetriaminepentaacetic acid (0.5 μmolar). Dye-providing composition B was the same except the 4'-hydroxyacetanilide was present at 5 mmolar, and in dye-providing composition C it was present at 2 mmolar.

The dye stop solution comprised sodium azide (0.1%) in phosphate buffered saline solution.

Wash composition A comprised TERGITOL TM 4 anionic surfactant (5%) in succinic acid (0.1 molar, pH 5). Wash composition B comprised decyl sulfate (1.8%) in sodium phosphate buffer (0.1 molar, pH 7.3). Wash composition C comprised TERGITOL TM 4 anionic surfactant (5%) in glycine buffer (0.1 molar, pH 10). Wash composition D comprised TERGITOL TM 4 anionic surfactant (5%) and casein (0.5%) in glycine buffer (0.1 molar, pH 10).

An extraction composition comprised EMCOL TM CC9 cationic surfactant (5%, Witco Chemical Co.) and sodium dodecyl sulfate (5%) in glycine buffer (0.1 molar, pH 8.5). The final antigen concentration after sample treatment was about $1.25 \times 10^8$ cells/ml in 450 μl.

Blocking solution A of a non-immunoreactive blocking protein comprised AMIDEK TM 131 protease (2% w/v, Genencor International), sodium chloride (50 mmolar), calcium chloride-$2H_2O$ (5 mmolar), 1,2-propanediol (10%) and sodium azide (0.01%) in glycine buffer (0.1 molar, pH 10). Blocking composition B contained the same components in 2-(N-morpholino)ethanesulfonic acid buffer (10 mmolar, pH 6) and the protease was present at 0.8%.

Polyclonal antibodies directed against each of the three microorganisms *Actinobacillus actinomycetemcomitans* (*A.a.*), *Prevotella intermedia* (*P.i.*) and *Porphyromonas gingivalis* (*P.g.*) were prepared by intravenous injection of rabbits according to the protocol described in U.S. Ser. No. 468,393 (noted above). IgG fractions were prepared by ammonium sulfate precipitation, and stored at 4° C. in phosphate buffered saline solution (0.3–0.4% solution). The bacterial strains used to produce the antisera were supplied as viable cultures by H. S. Reynolds (SUNY, Buffalo School of Dentistry). Isolates were subcultured on anaerobic plates. The microorganisms were those identified by the deposit numbers of ATCC 43717, ATCC 43718 and ATCC 43719 for *A.a.* (serotypes A, B and C, respectively), ATCC 25611, NCTC 9336 and ATCC 49046 for *P.i.* (serotypes A, B and C, respectively) and ATCC 33277, ATCC 53978 and ATCC 53977 for *P.g.* (serotypes A, B and C, respectively). ATCC is the American Type Culture Collection in Rockville, Md., and the NCTC is the National Collection of Type Cultures in London, England.

Water-insoluble reagents were prepared by covalently binding antibodies to polymeric particles (1 μmeter average diameter) of poly[styrene-co-4-(2-chloroethylsulfonylmethyl)-styrene] (95.5:4.5 molar ratio) which had been prepared using the procedures of EP-A-0 323 692 (noted above). Covalent attachment was achieved by adding the antibodies (0.17 mg/ml of antibodies specific to each of the three serotypes of *A.a.*, 0.25 mg/ml of each of the three serotypes of *P.i.*, or *P.g.*) to a solution of borate buffer (0.05 molar, pH 8.5) in a test tube and mixing well. The polymeric particles (3% solids, 0.01 μm averate diameter) were added to the buffered mixture, and the resulting suspension was rotated end-over-end for 4 hours at room temperature to allow covalent attachment of the antibodies to the particles. The suspension was then centrifuged at 2800 rpm for 10 minutes. The supernatant was discarded and the pellet was suspended in glycine buffer (0.1%, pH 8.5) containing TWEEN TM 20 nonionic surfactant (0.1%, ICI Americas) and merthiolate (0.01%).

A coating suspension of the reagent described above (0.35% solids) was prepared to have polyacrylamide binder (5%), TWEEN TM 20 nonionic surfactant (0.1%), merthiolate (0.01%) and UVITEX TM optical brightener (0.0005%, Ciba-Geigy) in glycine buffer (0.1 molar, pH 8.5). Each reagent directed to a distinct antigen was coated in defined regions of the membrane in the test devices described above.

Enzyme-antibody conjugates were prepared using antibodies directed to each microorganism conjugated to horseradish peroxidase using the procedure of Yoshitake et al, *Eur. J. Biochem.*, 101, 395, 1979. Each conjugate composition comprised the conjugates (15 μg of *P.i.* serotype B antibodies per ml, 7.5 μg of *P.i.* serotype A or C antibodies per ml, and 10 μg of *P.g.* and *A.a.* each serotype antibodies per ml) added to a solution of casein [0.5%, from a 1% solution in 0.1 molar 3-(N-morpholino)propanesulfonic acid buffer, pH 7.5], TWEEN ™ 20 nonionic surfactant (0.3%), merthiolate (0.01%), 4'-hydroxyacetanilide (10 mmolar) in buffer (0.1 molar, pH 7.5). The solution was filtered through a 0.22 μmeter filter.

All other materials and reagents were obtained from Eastman Kodak Company or other commercial sources.

General Assay Protocol for Examples

The following general procedure was used in the examples except where noted.

The reagents of antibodies on polymeric particles were deposited and dried in defined zones of the membrane in SURECELL ™ test devices as described above. There were three zones, one each for reagents specific to *A.a.*, *P.i.* and *P.g.*

Antigens from the three microorganisms were extracted with the extraction composition at room temperature to provide a final concentration ($1.25 \times 10^8$ cells/ml) for Examples 1–4 in a solution including the protease, extraction solution and the antigen stock solution, and the same concentration of cells in the antigen solution only for Examples 5–13 in a 450 μl sample of extractant. Extraction occurred immediately upon mixing.

For examples 5–14, the sample of extractant was then mixed with the blocking composition (450 μl for Examples 5–12, 265–300 μl for Examples 13 and 14) at room temperature. The resulting mixture was then filtered through a LOPRODYNE ™ microporous filtration membrane (1.2 μm average pore size, Pall Corporation) before use.

The filtered mixture was added to the test wells of the test devices containing the antibody reagents and allowed to drain through the membranes. Antibody conjugate composition (80 μl) was added to each test well, followed by incubation for 2 minutes at room temperature (about 18°–25° C.). A wash solution (500 μl) was then added to each test well, and allowed to drain. The washing was repeated. Dye-providing composition (80 μl) was added to each test well followed by a 1 minute incubation at room temperature. The resulting dye signals in the distinct zones on the membrane were then visually evaluated and compared to a calibrated color chart having reflectance density values. These values were converted to transmission density using the conventional Williams-Clapper transformation (*J. Opt. Soc. Am.*, 43, 595, 1953). $D_T$ values of 0.003 or less correspond to a visual evaluation of "no dye signal".

The entire assay protocol, from extraction to evaluation of the dye signal on the membrane, required less than about 5 minutes and was carried out entirely at room temperature.

EXAMPLES 1 & 2

Use of Blocking Composition Before or After Extraction in the Determination of Porphyromonas Gingivalis These examples demonstrate the use of the blocking composition both before and after extraction of antigen from *P.g.* The invention is compared to assays carried out without the use of a blocking composition. The use of two different wash solutions in combination with this invention was also evaluated.

Antigen was extracted from the microorganism as described above ($1.25 \times 10^8$ cells/ml). The protocol noted above was used for the assays, except in Example 1 where the blocking composition was added to the extraction composition prior to the extraction step. When this was done, blocking composition (100 μl) was mixed with tris(hydroxymethyl)aminomethane buffer (20 μl) and antigen solution (100 μl), then combining this mixture with the extraction composition (600 μl).

When the blocking composition was added to the extraction composition after the extraction step, the extraction composition (300 μl) was first mixed with the antigen solution (100 μl). After extraction of antigen, the blocking composition (400 μl) and tris(hydroxymethyl)amino-methane buffer (40 μl) were added. The Control sample containing no blocking protein was prepared from antigen solution (100 μl), phosphate buffered saline solution (100 μl) and extraction composition (600 μl).

A high pH was maintained in all assays by adding tris(hydroxymethyl)aminomethane buffer (1.65 molar, pH 10–12) to the mixture of blocking composition and extraction composition. Each mixture was then filtered through a microporous filtration membrane (1.2 μm average pore size), and divided equally for use in the assays. Wash compositions A and B were used in the assays. Dye-providing composition A was used in all assays.

The assays are identified herein as follows:

Control A: No blocking composition used, wash solution B.

Control B: No blocking composition used, wash solution A.

Control C: Blocking composition B added before extraction, wash solution B.

Control D: Blocking composition B added after extraction, wash solution B.

Example 1: Blocking composition B added before extraction, wash solution A.

Example 2: Blocking composition B added after extraction, wash solution A.

The resulting dye signals in the distinct zones [one zone each for reagents specific for *P.i.*, *A.a.* and *P.g.*] on the membrane were evaluated as described above, and are recorded in Table I below. The results indicate that Controls A and B utilizing no blocking protein had unacceptably high "apparent" cross-reactivity of *P.g.* antigen with antibodies to the other microorganisms, even though the overall signal was significantly reduced in Control B using the TERGITOL ™ 4 anionic surfactant in the wash composition.

The results further indicate that the blocking protein can be mixed with antigen either before or after extraction to reduce cross-reactivity while providing high sensitivity to the extracted antigen (*P.g.*). It is preferred for lowest cross-reactivity to mix them after extraction (Example 2).

TABLE I

| Assay | Dye Signal ($D_T$) | | |
|---|---|---|---|
| | *P.i.* Reagent | *A.a.* Reagent | *P.g.* Reagent |
| Control A | 0.114 | 0.114 | 0.185 |
| Control B | 0.019 | 0.019 | 0.145 |
| Control C | 0.114 | 0.114 | 0.185 |
| Control D | 0.114 | 0.114 | 0.185 |

TABLE I-continued

| Assay | Dye Signal ($D_T$) | | |
|---|---|---|---|
| | P.i. Reagent | A.a. Reagent | P.g. Reagent |
| Example 1 | 0.007 | 0.007 | 0.160 |
| Example 2 | 0.003 | 0.003 | 0.145 |

EXAMPLE 3

Assay for *P. gingivalis* Using Higher pH

This example is similar to the assays of Examples 1 and 2 except that the mixture of extractant and blocking composition was at pH 9.0–9.3. The blocking composition noted above (400 μl) and tris(hydroxymethyl)aminomethane buffer (40 μl) were added to the extractant (400 μl) to form a mixture for the assays.

In the Control E assay, no blocking composition was used, and wash composition A was used. The Control F assay was similar except that wash composition B was used. In the Control G assay, blocking composition was used with wash composition B. In Example 3, blocking composition was used with wash composition A. Dye-providing composition A was used in all assays.

The results are shown in Table II below. The lowest cross-reactivity was achieved with the assay of Example 3.

TABLE II

| Assay | Dye Signal ($D_T$) | | |
|---|---|---|---|
| | P.i. Reagent | A.a. Reagent | P.g. Reagent |
| Control E | 0.019 | 0.019 | 0.145 |
| Control F | 0.145 | 0.145 | 0.185 |
| Control G | 0.145 | 0.145 | 0.185 |
| Example 3 | 0.003 | 0.003 | 0.145 |

EXAMPLE 4

Assays Using Extractions at Various pH Values

The assay of this invention using blocking composition B was compared to similar assays whereby the pH of the extraction composition was varied or tris (hydroxymethyl)-aminomethane buffer was omitted. Thus, the pH of the resulting mixture of extraction composition and blocking composition was varied. Wash composition A and dye-providing composition A were used in the assays.

The assays had the following parameters:

Control H: Extraction composition had pH of 5.2 and was mixed with blocking composition B, but no buffer was used to adjust the pH so the final pH was 6.6–7.2.

Control I: Extraction composition had pH of 8.5, blocking composition B and buffer omitted.

Control J: Extraction composition had pH of 8.5 was mixed with blocking composition B, but no buffer was used to adjust the pH so the final pH was 8.2.

Control K: Extraction composition had a pH of 8.5 was mixed with buffer, but the blocking composition B was omitted so the final pH was 9.3.

Example 4: Extraction composition had a pH of 8.5 was mixed with blocking composition B and buffer to give a final pH of 9.3.

The data from the assays are seen in Table III below. It is clear that the final pH of the mixture of blocking composition and extraction composition is important in eliminating "apparent" cross-reactivity in the assays. Increasing the pH above about 8 helped to reduce the "apparent" cross-reactivity while maintaining sensitivity to the antigen of interest. The optimum performance was obtained using the blocking composition at pH above about 9. Increasing the pH above 9 without the use of the blocking composition, however, did not sufficiently reduce the "apparent" cross-reactivity.

TABLE III

| Assay | Final pH | Dye Signal ($D_T$) | | |
|---|---|---|---|---|
| | | P.i. Reagent | A.a. Reagent | P.g. Reagent |
| Control H | 6.6–7.2 | 0.019 | 0.019 | 0.175 |
| Control I | 8.5 | 0.057 | 0.057 | 0.160 |
| Example 4 | 9.3 | 0.003 | 0.003 | 0.175 |
| Control J | 8.2 | 0.015 | 0.013 | 0.175 |
| Control K | 9.3 | 0.057 | 0.057 | 0.175 |

EXAMPLES 5–9

Use of Casein As Blocking Protein

Examples 5–8 show the use of casein as a blocking protein in the assays of this invention. Various concentrations of the protein were tried. Example 9 again shows the use of a protease (AMIDEK ™ 131 protease) as the blocking protein. Control L was an assay using a buffer as the "blocking composition".

In these assays, a specimen (450 μl) containing *P. gingivalis* antigen was mixed with the blocking composition (450 μl) and the resulting mixture was filtered through a 1.2 μmeter filter prior to use in the assay. The pH of the resulting mixture was 9.3. Wash solution C and dye-providing composition B were used in the assays. The blocking compositions containing various amounts of casein (0.25% for Example 5, 0.5% for Example 6, 0.75% for Example 7 and 1% for Example 8), or protease (1% AMIDEK ™ 131, Example 9) also contained sodium chloride (50 mmolar), calcium chloride-2$H_2O$ (5 mmolar), sodium azide (0.01%) and 1,2-propanediol (10%) in glycine buffer (100 mmolar, pH 10).

The results of the assays are shown in Table IV below. They indicate that casein is also effective as a blocking protein in the practice of this invention to reduce cross-reactivity, although the use of the protease (Example 9) is preferred to provide greater sensitivity to the antigen of interest.

TABLE IV

| Assay | Dye Signal ($D_T$) | | |
|---|---|---|---|
| | P.i. Reagent | A.a. Reagent | P.g. Reagent |
| Example 5 | 0.007 | 0.008 | 0.101 |
| Example 6 | 0.003 | 0.005 | 0.101 |
| Example 7 | 0.003 | 0.005 | 0.101 |
| Example 8 | 0.003 | 0.005 | 0.101 |
| Example 9 | 0.003 | 0.007 | 0.175 |
| Control L | 0.019 | 0.019 | 0.175 |

EXAMPLES 10–12

Use of Bovine Serum Albumin As a Blocking Protein

Examples 10 and 11 show the use of a serum protein, that is bovine serum albumin (1% and 2%, respectively), as a blocking protein in the practice of this invention. Example 12 again shows the use of a protease (AMIDEK ™ 131 protease composition of Example 9) as a preferred blocking protein. The other components in the blocking compositions were the same as shown in Examples 5–9. The Control M assay used no blocking composition. Dye-providing composition C and wash composition D were used in these assays.

The results are listed in Table V below. While the data show that bovine serum albumin does not provide results better than the preferred protease, it does provide a desirable improvement in reducing "apparent" cross-reactivity.

TABLE V

| | Dye Signal ($D_T$) | | |
|---|---|---|---|
| Assay | P.i. Reagent | A.a Reagent | P.g. Reagent |
| Example 10 | 0.024 | 0.024 | 0.114 |
| Example 11 | 0.025 | 0.025 | 0.130 |
| Example 12 | 0.003 | 0.005 | 0.145 |
| Control M | 0.057 | 0.057 | 0.175 |

EXAMPLE 13

Preferred Embodiment of the Invention

This example represents the preferred assay of this invention whereby an antigen extracted from P. gingivalis was detected using the blocking composition A. Wash composition D and dye-providing composition C were used. The mixture of blocking composition and extractant had a pH of about 9.3 when it was added to the test wells of the test devices. The Control N assay was carried out without using a blocking composition.

The results of the assays are shown in Table VI below.

TABLE VI

| | Dye Signal ($D_T$) | | |
|---|---|---|---|
| Assay | P.i. Reagent | A.a. Reagent | P.g. Reagent |
| Control N | 0.019 | 0.019 | 0.175 |
| Example 13 | 0.003 | 0.007 | 0.175 |

EXAMPLE 14:

Detection of Three Microorganisms

The present example illustrates the practice of this invention to determine various concentrations of antigen extracted from A.a., P.g. and P.i. The assay was carried out using the protocol described above. The solutions of extracted antigen were mixed with a composition containing AMIDEK TM protease (Genencor International, Rochester, N.Y.) (300 μl of 20 mg/ml solution) for a few seconds at room temperature prior to adding the antigen to the test wells of the test devices. Dye-providing composition B was used in this example, and the volume of antibody conjugate was a 80 μl sample.

The wash composition comprised TERGITOL TM 4 anionic surfactant (1.35%), casein (0.5%) and thimerosal (0.1%) in glycine buffer (0.1 molar, pH 10).

Antigen was extracted from P.g. serotypes A, B and C, P.i., serotype A and A.a., serotype B. Antigen concentrations tested were $1.25 \times 10^8$ cells/ml, $1.56 \times 10^7$ cells/ml and $1.95 \times 10^6$ cells/ml for P.g. and P.i. and $6.25 \times 10^7$ cells/ml, $3.91 \times 10^6$ cells/ml and $4.88 \times 10^5$ cells/ml for A.a.

The results of the assays are tabulated in Table VII below. They illustrate the use of the present invention to detect three different microorganisms associated with periodontal diseases and they show that the use of the protease does not interfere with the detection of each of the three microorganisms. The use of a protein pretreatment aids in the elimination of cross-reactivity particularly when high antigen concentrations are used.

TABLE VII

| | | | $D_T$ Dye Signal | | |
|---|---|---|---|---|---|
| Antigen | Cell Concentration | Assay | P.g. Reagent | P.i. Reagent | A.a. Reagent |
| P.g. Serotype A | $1.25 \times 10^8$ cells/ml | Example 14 | 0.175 | 0.007 | 0.011 |
| P.g. Serotype A | $1.56 \times 10^7$ cells/ml | Example 14 | 0.114 | 0.003 | 0.003 |
| P.g. Serotype A | $1.95 \times 10^6$ cells/ml | Example 14 | 0.019 | 0.003 | 0.003 |
| P.g. Serotype C | $1.25 \times 10^8$ cells/ml | Example 14 | 0.185 | 0.003 | 0.003 |
| P.g. Serotype C | $1.56 \times 10^7$ cells/ml | Example 14 | 0.160 | 0.003 | 0.003 |
| P.g. Serotype C | $1.95 \times 10^6$ cells/ml | Example 14 | 0.011 | 0.003 | 0.003 |
| P.g. Serotype B | $1.25 \times 10^8$ cells/ml | Example 14 | 0.195 | 0.003 | 0.003 |
| P.g. Serotype B | $1.56 \times 10^7$ cells/ml | Example 14 | 0.114 | 0.003 | 0.003 |
| P.g. Serotype B | $1.95 \times 10^6$ cells/ml | Example 14 | 0.024 | 0.003 | 0.003 |
| P.i. Serotype A | $1.25 \times 10^8$ cells/ml | Example 14 | 0.003 | 0.175 | 0.003 |
| P.i. Serotype A | $1.56 \times 10^7$ cells/ml | Example 14 | 0.003 | 0.114 | 0.003 |
| P.i. Serotype A | $1.95 \times 10^6$ cells/ml | Example 14 | 0.003 | 0.024 | 0.003 |
| A.a. Serotype B | $6.25 \times 10^7$ cells/ml | Example 14 | 0.003 | 0.003 | 0.175 |
| A.a. Serotype B | $3.91 \times 10^6$ cells/ml | Example 14 | 0.003 | 0.003 | 0.101 |
| A.a. Serotype B | $4.88 \times 10^5$ cells/ml | Example 14 | 0.003 | 0.003 | 0.011 |

The invention has been described in detail with particular reference to preferred embodiments thereof, but it will be understood that variations and modifications can be effected within the spirit and scope of the invention. All patents, patent applications (published or unpublished, domestic or foreign), scientific literature, books and other prior art cited herein are each incorporated herein by reference for the teaching therein pertinent to this invention.

We claim:

1. A method for the determination of at least one microorganism associated with a periodontal disease comprising the steps of:
   A. in a specimen suspected of containing said microorganism, extracting an antigen from said microorganism using an extraction composition which is buffered to a pH of at least about 8,
   B. simultaneously with or immediately after extraction in step A, mixing said extraction composition with a blocking composition to reduce nonspecific interactions, said blocking composition having a pH of from about 8.5 to about 11.5 and consisting essentially of a non-immunoreactive blocking protein in an amount sufficient to provide a mixture having at least about 0.2 weight percent of said protein, said protein being casein or a protease,
   C. while maintaining the pH of the mixture formed in step B at from about 8.5 to about 11.5, contacting said mixture with an antibody specific to said antigen to form an immunological complex, and
   D. detecting said complex as an indication of the determination of said microorganism in said specimen.

2. The method of claim 1 wherein said microorganism is *Actinobacillus actinomycetemcomitans*, *Porphyromonas gingivalis* or *Prevotella intermedia*.

3. The method of claim 1 wherein more than one microorganism associated with periodontal disease is detected and differentiated in step D by adding an antibody specific for antigen extracted in step A from each microorganism.

4. The method of claim 1 wherein said non-immunoreactive protein is present in said mixture formed in step B in an amount of from about 0.2 to about 1 weight percent.

5. The method of claim 1 wherein said non-immunoreactive blocking protein is a protease which is an analog of a *Bacillus subtilis* protease having an amino acid sequence comprising an Asn-Gly sequence wherein one or both amino acid residues of said sequence are deleted or replaced by a residue of a different amino acid.

6. The method of claim 5 wherein said Asn residue of said sequence is replaced with a serine residue in the 109 and 218 amino acid positions.

7. The method of claim 1 wherein said antibody is immobilized on a water-insoluble substrate, and said immunological complex further comprises a second antibody specific for said antigen, said second antibody being water-soluble and detectably labeled.

8. The method of claim 7 wherein said second antibody is labeled with an enzyme, and said immunological complex is detected using a composition which provides a colorimetric, fluorometric or chemiluminescent signal in the presence of said enzyme.

9. A method for the determination of at least one microorganism associated with a periodontal disease comprising the steps of:
   A. extracting an antigen from said microorganism which is present in a specimen, using an extraction composition which is buffered to a pH of from about 8.5 to about 11.5,
   B. simultaneously with or immediately after the extraction in step A and without lowering the pH of the extraction composition below about 8, mixing said extraction composition with a blocking composition to reduce nonspecific interactions, said blocking composition consisting essentially of a non-immunological blocking protein in an amount sufficient to provide a mixture having at least about 0.2 weight percent of said protein, said protein being casein or a protease, the pH of said mixture being at from about 8.5 to about 11.5,
   C. contacting said mixture formed in step B with a microporous membrane having thereon, in a discrete zone of a surface of said membrane, a water-insoluble reagent comprising water-insoluble particles having affixed thereto antibodies specific to said extracted antigen, to form in said zone, a water-insoluble complex between said antibody and the extracted antigen on said membrane,
   D. prior to, simultaneously with or immediately subsequent to the contact in step C, but after step B, contacting said extracted antigen with a detectably labeled, water-soluble second antibody specific to said extracted antigen so as to form a detectably labeled, water-insoluble sandwich complex specific for said microorganism, the complex being formed from both said water-soluble labeled and water insoluble antibodies with said extracted antigen in said zone on said membrane,
   E. simultaneously with or subsequently to step D, washing uncomplexed materials through said membrane, and
   F. detecting said labeled, water-insoluble sandwich complex in said zone on said membrane as a determination of said microorganism in said specimen.

10. The method of claim 9 wherein three or more microorganisms associated with periodontal disease or serotypes thereof are detected and differentiated in step F simultaneously in three or more distinct zones on said membrane by adding to each of said distinct zones an antibody specific for antigen extracted in step A from each of said microorganisms.

11. The method of claim 10 wherein said microorganisms detected and differentiated are among *Actinobacillus actinomycetemcomitans, Porphyromonas gingivalis* and *Prevotella intermedia.*

12. The method of claim 9 wherein said membrane has an average pore size of from about 0.4 to about 5 μmeters, and said water-insoluble particles have an average diameter of from about 0.01 to about 10 μmeters.

13. The method of claim 9 wherein said water-soluble antibodies are labeled with a radioisotope, enzyme or biotin.

14. The method of claim 13 wherein said label is an enzyme, and detection is accomplished using a composition which provides a colorimetric, fluorometric or chemiluminescent signal in the presence of said enzyme.

15. The method of claim 9 wherein said non-immunoreactive protein is a protease which is an analog of a *Bacillus subtilis* protease having an amino acid sequence comprising an Asn-Gly sequence wherein one or both amino acid residues of said sequence are deleted or replaced by a residue of a different amino acid.

16. The method of claim 15 wherein said Asn residue of said sequence is replaced with a serine residue in either or both of the 109 and 218 amino acid positions.

17. A diagnostic test kit comprising, in separate packaging:
   (a) an extraction composition buffered to a pH of at least about 8,
   (b) a composition consisting essentially of a non-immunoreactive blocking protein buffered to a pH of from about 8.5 to about 11.5, said blocking protein selected from the group consisting of casein and a protease, and
   (c) a water-soluble antibody specific for an antigen present in a microorganism associated with a periodontal disease.

18. The kit of claim 17 further comprising at least one kit component selected from the group consisting of:
   (d) a disposable test device comprised of a microporous filtration membrane having disposed thereon an antibody specific for an antigen present in a microorganism associated with a periodontal disease, said membrane having an average pore size of from about 0.4 to about 5 μmeters,
   (e) a wash composition for separating uncomplexed materials from a complex of said antigen and antibody, said composition comprising at least one surfactant, and
   (f) a composition for providing a colorimetric, fluorometric or chemiluminescent signal in the presence of an enzyme label.

* * * * *